(12) United States Patent
Brock et al.

(10) Patent No.: US 7,538,336 B2
(45) Date of Patent: May 26, 2009

(54) AUTOMATIC IDENTIFICATION OF REAGENT TEST STRIPS USING REFLECTANCE VALUES

(75) Inventors: David A. Brock, Elkhart, IN (US); Chris T. Zimmerle, Goshen, IN (US); David J. Ledden, Medway, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 10/556,097

(22) PCT Filed: Jun. 3, 2004

(86) PCT No.: PCT/US2004/017339

§ 371 (c)(1),
(2), (4) Date: Dec. 26, 2006

(87) PCT Pub. No.: WO2005/001453

PCT Pub. Date: Jan. 6, 2005

(65) Prior Publication Data

US 2007/0278431 A1   Dec. 6, 2007

Related U.S. Application Data

(60) Provisional application No. 60/475,288, filed on Jun. 3, 2003.

(51) Int. Cl.
*G01N 21/86* (2006.01)

(52) U.S. Cl. .............................. 250/559.4; 250/559.44

(58) Field of Classification Search ............ 250/559.04, 250/559.05, 559.07, 559.29, 559.39, 559.44, 250/555; 436/43, 45, 46, 47; 356/445, 429, 356/402, 425; 435/7.1, 14, 285.2, 283.1; 702/28, 85
See application file for complete search history.

(56) References Cited

U.S. PATENT DOCUMENTS

| | | | |
|---|---|---|---|
| 4,592,893 A | 6/1986 | Poppe et al. | 422/56 |
| 5,126,952 A | 6/1992 | Kildal-Brandt et al. | 364/571.02 |
| 5,877,863 A | 3/1999 | Ross et al. | 356/445 |
| 5,945,341 A | 8/1999 | Howard, III | 436/46 |
| 7,267,799 B1 * | 9/2007 | Borich et al. | 422/82.05 |
| 2003/0049849 A1 * | 3/2003 | Mori et al. | 436/46 |

FOREIGN PATENT DOCUMENTS

| | | |
|---|---|---|
| EP | 0 646 784 A | 4/1995 |
| EP | 0 837 320 A | 4/1998 |
| EP | 1 118 859 A | 7/2001 |
| WO | 98/32004 A | 7/1998 |
| WO | 99/41596 A | 8/1999 |

* cited by examiner

*Primary Examiner*—Que T Le
(74) *Attorney, Agent, or Firm*—McDermott Will & Emery LLP (57) ABSTRACT

Identifying a test product having a test region includes impinging on the test region a set of test signals at known test wavelengths. An image of the test region is generated from the reflected signals. The image is comprised of a set of reflectance values that are compared against reference reflectance values at the test signal wavelengths to determine the test product type.

33 Claims, 6 Drawing Sheets

AUTOMATIC IDENTIFICATION OF REAGENT TEST STRIPS USING REFLECTANCE VALUES

CROSS REFERENCES TO RELATED APPLICATIONS

This application claims the benefit of priority under 35 U.S.C. §119(e) from co-pending, commonly owned U.S. provisional patent application Ser. No. 60/475,288, entitled DIAGNOSTIC INSTRUMENT, filed Jun. 3, 2003.

FIELD OF THE INVENTION

The inventive concepts relate to systems and methods for automated identification and/or confirmation of reflectance-based reagent test products. More particularly, the present invention relates to systems and methods for performing automatic identification and/or confirmation of reagent test products using reflectance values.

BACKGROUND

In a wide variety of medical and laboratory applications, reflectance-based systems, often referred to as "reflectometers" are used to perform tests. In a typical form, a reflectometer includes one or more light sources configured to generate one or more light signals at given wavelengths. An object under test receives the signal and reflects a portion thereof. One or more detectors or sensors are oriented to receive the reflected signals. A processor analyzes the characteristics of the received reflected signals and produces a test result.

Such reflectometers are sometimes used for performing tests on a reagent test strip. In such a case, the test pads on the test strip may be incrementally tested to determine the presence of analytes in a liquid test sample absorbed into the test pads. Such systems may be used for performing urinalysis tests, as one example. That is, the level or presence of an analyte in a liquid test sample can be determined by causing a given test pad to absorb some of the liquid test sample, (e.g., a sample of urine) and then by reading associated reflectance values for the test pad with a reflectometer. Based on the reflectance characteristics of the signal reflected by the test pad, the reflectometer determines the presence or level of the analyte in a given test pad. As an example, a test pad changes color to indicate the level or presence of the analyte in response to absorption of urine from a urine sample. The characteristics of a reflected signal are a function of the make-up and color of the test pad and the wavelength of the light source. Consequently, a change in color of a test pad causes a corresponding change in the characteristics of the reflected signal.

Test strips are typically produced according to industry accepted formats. In the case of urinalysis reflectometers, test strips can come in formats having different lengths, such as, for example, 3.25 inch lengths or 4.25 inch lengths. Within each format, a test strip is defined according to its configuration, i.e., the number, types and order of test pads included on the test strip. Generally, each test strip configuration is uniquely identified. Implicit in a test strip identification and/or confirmation, therefore, is the test strip format and the test pad configuration. As will be appreciated by those skilled in the art, such test pads may include, for example, pH, ketone, nitrite, and glucose test pads. In order for the reflectometer to produce valid results, the test strip must be identified by format and configuration, so that the reflectometer has a proper context to evaluate the received reflected signals, or reflectance values derived therefrom. That is, a reflectometer needs to know that a received reflected signal is produced by, for example, a glucose test pad or a ketone test pad.

Reagent cassettes can also be tested using a reflectometer, in a manner very similar to that used for the test strip. Such reagent cassettes include a test region that provides visual indications of test results, similar to the test pads of the test strips. The test region can produce a series of lines that embody the test results.

There is a variety of known ways that the test strip is identified to or by the reflectometer. In some reflectometers, an operator enters data into the reflectometer that indicates the identification of the test strip from a look up table, or chooses the identification from a set of predefined options. The same can be done for reagent cassettes. The reflectometer is then ready to process the test strip or cassette. Other reflectometers include more automated mechanisms for determining the identification of the test strip. As described below, these various prior art automated reflectometers have certain drawbacks.

U.S. Pat. No. 4,592,893, as an example, discloses a test strip having a test field and a separate bar code for storing batch-specific information necessary for the quantitative evaluation of the reactions carried out on the test field. A narrow bar in the bar code is interpreted as logical 0 and a wide bar is interpreted as a logical 1. The binary code embodied in the bar code corresponds to the batch-specific information imputed to the test strip.

U.S. Pat. No. 5,126,952, as another example, discloses a method of providing data in a bar code form on a test strip useful for the determination of a lot of test elements for use in a chemical analyzer. A calibration curve corresponds to a given formula and its solution for a given lot of test elements is represented in a single bar code strip of only a few digits that accurately provide a calibration code for that lot of test elements.

U.S. Pat. No. 5,945,341, owned by Bayer Corporation of Elkhart, Ind., discloses an automated approach to reading a test strip wherein at least one test field and at least two marker fields are included on the test strip. The marker fields reflect light at specific ranges of wavelengths which differ from each other in a coded sequence of spectral regions that correlate to information about the test strip. A test strip reading device reads spectral reflectance values from the test and marker fields individually to identify the test strip, i.e., by moving the test strip with respect to a reading means.

The automated approaches for determining the identification of or information about a test strip provided to date require non-standard modifications to include bar codes, marker fields, test fields or some combination thereof. In some cases, there is no ability to add a bar code to an existing test strip. Therefore, certain non-standard test strips may only lend themselves to automated identification in certain non-standard reflectometers. And, certain standard test strips may not be identifiable by such automated systems. Even in properly equipped devices, the process of reading such fields can require multiple readings of the various areas of the strip to determine its identification. For the most part, operators of such reflectometers are required to have at least a minimum skill level necessary to identify test strips and conduct tests, in some cases certain certifications may also be desired. Identification of the test strips is required to achieve accurate and reliable test results. Systems tailored for specialized non-standard approaches tend to increase complexity.

It would be advantageous to eliminate some of the complexity inherent in such prior art approaches. In doing so, the required skill level, and possibly certifications, of the operator may be reduced. It would also be advantageous to provide a system and method that are not inherently limited to a subset of non-standard identification approaches, such as bar codes, test fields, marker fields or various differing implementations of the foregoing.

SUMMARY OF THE INVENTION

An automated test product identification system and method are provided for identifying or confirming the identity of a reagent test product, such as test strips or cassettes for use in a reflectometer. In accordance with the present invention, a substantial portion of, if not the entire, test product may be imaged at one time. Bar codes, test fields, or marker fields may be included, but need not be relied on for identification of the test product.

A test strip includes a region of interest comprising a plurality of test pads, the type and order of which determine the configuration of the test strip. The present invention avoids the prior art need for multiple or incremental readings of the test strip or its pads or the need for the reading of bar codes, test fields, or marker fields on the test strip.

A reagent cassette can include a bar code or other markings that indicate the type of cassette. As discussed with respect to test strips, a reagent cassette comprises a region of interest to be imaged. The region of interest includes a test window that frames a reagent test area, similar to the test pads, and may also include identification markings. The same functional elements that can be used to identify or confirm the identity of a test strip can also be used with a reagent cassette, as discussed below.

Any of a wide variety of test products can be accommodated in a single system. Many of such test products may be of a standard format, but non-standard test products may also be accommodated, so long as they are defined to the test product identification system. Accordingly, the system may include a database of stored test product identification information, network or remote access to such information, or some combination thereof. A user interface may be included to accommodate entry of test product definitions and information and selection of predefined test products. The test product information includes data indicative of a plurality of reference test products and of a plurality of sets of associated reference reflectance values. Each reflectance value may be associated with a wavelength and the material reflecting the test signal.

A test product identification system or module may be standalone, integral with or coupled to a reflectometer. For purposes of this description, it is assumed that the reflectometer includes the test product identification system. Therefore, the reflectometer could include test product identification software, hardware, firmware or some combination thereof for implementing a method for identifying and/or confirming the identification of a test product. Software may be provided as computer code, programs, or modules executing on one or more processors.

A test product identification system in accordance with the present invention includes a set of one or more test signal generators is configured to generate a set of test signals having known wavelengths. As an example, the system may include one or more LEDs for generation of the test signals, wherein each LED can be configured to transmit light at a different a wavelength.

One or more detectors is provided and configured to detect signals reflected from the test pads. The detectors may be configured to create a pixel-based image of the test product from the reflected signals, wherein the pixel-based image may comprise a plurality of pixel sets and each pixel set may correspond to a different test pad on a test strip or test area of a reagent cassette.

A translator is configured to determine a reflectance value from the pixel-based image for each test pad or reagent cassette test area. The reference reflectance values may be derived from a set of spectral signatures, wherein each of the spectral signatures is associated with a reference test pad type and includes a reference reflectance value at each of a plurality of wavelengths.

A pad typing module is configured to compare the reflectance values with the sets of reference reflectance values for the test signal wavelength to determine a test pad type for each test pad imaged. The pad typing module may also be configured to determine a test pad count as a function of the pixel-based image. The pad typing module may be further configured to determine a test strip format as a function of the test pad count. The pad typing module may also be configured to determine a test pad order as a function of said reflectance values and may be further configured to apply a selected subset of reference reflectance values to each test pad as a function of a test pad's position in the test pad order and the set of test strips defined to the system. For example, if pad 1 is being analyzed and there are no defined test strips that have a nitrite pad as pad 1, then the reference reflectance values for the nitrite test pad need not be part of the analysis for determining the test pad type for pad 1.

An identification module is configured to identify or confirm the identity of the test strip as a function of the test pad types and the order of the test pads, which is also determined from the pixel-based image. Or, in the case of a reagent cassette, the identification module may determine or confirm the identity of the reagent cassette as a function of an image of its test area, markers or bar codes, or some combination thereof.

If the system is unable to identify or confirm the identity of a test strip or reagent cassette an indication is provided to the user. Such indication may take the form of an output, such as an error message being provided via a graphical user interface.

The system may further comprise a test conduct module configured to determine a test result for test product as a function of the received reflectance values. In the case of a test strip, the test results can be provided for one or more of the test pads. In the case of a reagent cassette, the test conduct module determines test results from an image of the reagent test area exposed in the test window of the cassette.

BRIEF DESCRIPTION OF THE DRAWINGS

The drawing figures depict preferred embodiments by way of example, not by way of limitations. In the figures, like reference numerals refer to the same or similar elements.

DETAILED DESCRIPTION OF THE PREFERRED EMBODIMENTS

An automated test product identification system and method are provided for identifying test products, such as those configured for use in a reflectometer—for example, that described in U.S. Pat. No. 5,877,863 owned by Bayer Corporation, Elkhart, Ind. Such test products may include reagent test strips or cassettes. In accordance with the present invention, a region of interest of a test product is imaged at one time. Therefore, the present invention avoids the prior art need for multiple readings of a test product or the need for the reading of bar codes, test fields, or marker fields on the test product. Bar codes, test fields, or marker fields may be included on the test product, but need not be relied on for identification. Consequently, any of a wide variety of defined test products can be accommodated in a single system.

Many of such test products may be of a standard format, but non-standard test products may also be accommodated, so long as they are defined to the test product identification system. Accordingly, the test product identification system may include a database of stored test strip and reagent cassette identification information, network or remote access to such information, or some combination thereof. The test product identification system may also include a user interface to accommodate entry of test product definitions and information, such as types and formats of test strips and reagent cassettes. The user interface may also provide a means for selection of a test product type from any of the foregoing storage means.

A test product identification system or module may be standalone or integral with or coupled to a reflectometer. For purposes of this description, it is assumed that the reflectometer includes the test product identification system, e.g., test product identification software implementing a method for identifying and/or confirming the identification of a test strip or reagent cassette.

Figure 1:
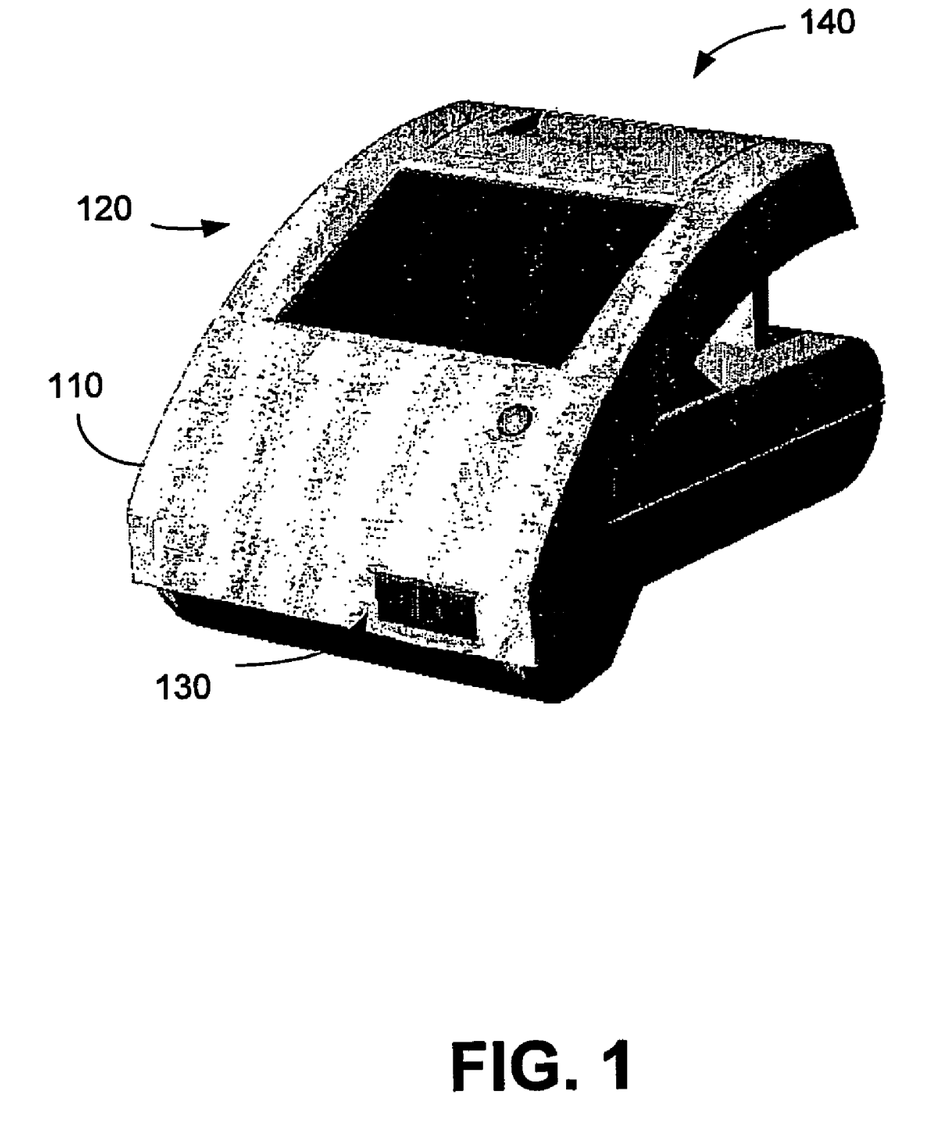
FIG. 1 is a perspective of a reflectometer in accordance with the present invention.

FIG. 1 provides a perspective view of an embodiment of a reflectometer 100 in accordance with the present invention. Reflectometer 100 provides an input and output device in the form of a touch screen 120. As will be appreciated by those skilled in the art, other forms of input and output mechanisms may be used. For example, reflectometer 100 may be configured to coupled by wired or wireless means to a personal computer, handheld computer, network, monitor, printer, audio/visual system or the like. A housing 110 houses the touch screen 120, as well as a variety of internal functional elements. An input port 130 is provided to facilitate insertion of one or more test strips or reagent cassettes via a carriage. An output port 140 provides a means for printing a report (e.g., test or diagnostic report) to an operator or user of reflectometer 100.

Figure 2:
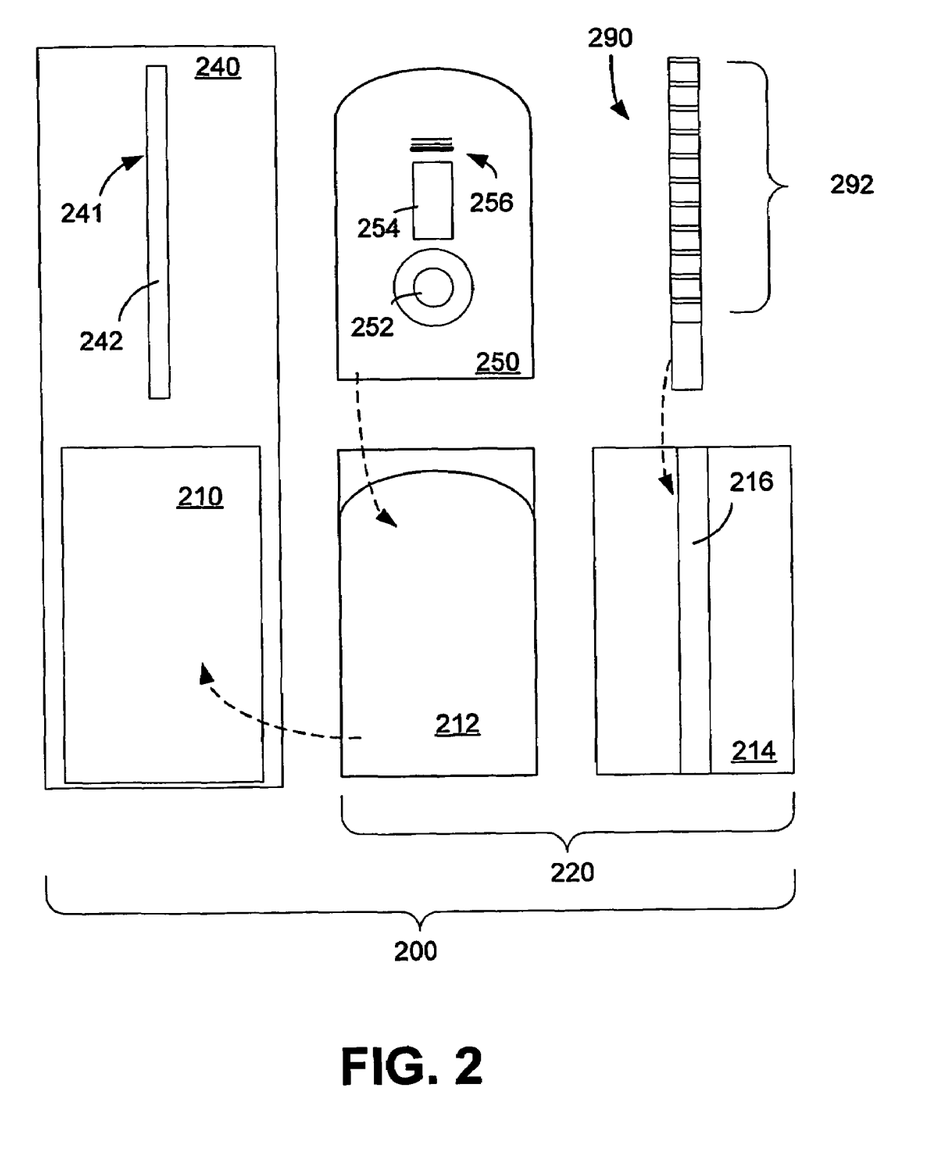
FIG. 2 is a view of a carriage used with the spectrometer of FIG. 1, including a view of a insert used with the carriage for accommodating various test strips.

Referring to FIG. 2, a collection of test product insertion components 200 for use with reflectometer 100 is shown. A carriage 240 is configured for insertion in input port 130 of the reflectometer 100, with a test product. Carriage 240 includes an insert region 210 within which a test product insert 220 configured to hold a test product (e.g., a reagent test strip 290 or cassette 250) may be placed. In the preferred form, insert 220 includes a first side 214 configured to hold the reagent test strip 290 within a slot 216. Representative test strip 290 includes a plurality of test pads 292, the configuration of which depends on the particular test strip type. The insert 220 may be loaded into carriage 240 and then test strip 290 is positioned within slot 216, such that side 214 available for imaging. Carriage 240 may be configured to accommodate a test strip of any of a variety of lengths, such as test strips of the 3.25" and 4.25" length formats, as examples.

A region of interest to be imaged may include one or more of test pads 292. In order for the test pads 292 to be imaged, those pads must be accessible by imaging components. Accordingly, in the embodiment of FIG. 2, test strip 290 is disposed within carriage 240 such that the test strip pads 292 are visible. A calibration bar 242 is also visible through an aperture 241 formed within insert 210. Calibration bar 242 provides a means of calibrating the light sources and detectors discussed below with respect to FIGS. 3A and 3B.

Insert 220 may optionally include a second side 212 configured to accept reagent cassette 250. Such reagent cassettes are known in the art. For instance, reagent cassette 250 may be a disposable, single-use hCG immunoassay cassette for performing a pregnancy test. The reagent cassette 250, as with the test strip 290, includes a region of interest that can be imaged to confirm or determine the identity of the cassette. The region of interest may include a test area defined by a window 254 and also include identification markings, such as bar codes 256. The reagent test area is viewable and capable of being imaged when the carriage is loaded into reflectometer 100. Beyond identification of the reagent cassette, the image may also be used to determine the test results.

The reagent cassette 250 has an opening or well 252 into which a body fluid sample, such as urine, is deposited. The fluid sample propagates to the test area defined by window 254. The reagent cassette test area comprises a test line area, reference line area and control line area, as is known in the art. Test results can take the form of one or more lines displayed in these areas. With introduction of a fluid sample, the reagent cassette test area may change color, for example, at least one colored stripe may appear in window 254.

As an example, the various components of FIG. 2 may take the form of those more fully described in co-owned and co-pending U.S. patent application Ser. No. 10/821,441, incorporated herein by reference.

The selection and orientation of test pads 292 on test strip 290 is generally according to a predetermined standard or format for the test strip. Table 1 shows a representative sampling of test strips, of the 4.25" format and of the 3.25" format. For the 4.25" format of test strips, pad 1 defines the last pad or tip of the test strip. For the 3.25" test strip format, pad 5 defines the tip of the test strip. In this example, the reagent code for each test pad, i.e., pads 1-11 for the 4.25" format and pads 5-11 for the 3.25" format, are given as follows: b=bilirubin, c=creatinine, g=glucose, k=ketone, m=microalbumin, n=nitrite, o=occult blood, p=protein, pH=pH, s=specific gravity, u=urobilinogen and w=leukocyte. For other test strips, the pads may be defined differently.

TABLE 1

| Product | Pad | | | | | | | | | | |
|---|---|---|---|---|---|---|---|---|---|---|---|
| | 1 | 2 | 3 | 4 | 5 | 6 | 7 | 8 | 9 | 10 | 11 |
| Strip A | | | | | g | p | pH | — | s | — | — |
| Strip B | | | | | n | p | g | — | o | — | — |
| Strip C | | | | | g | p | pH | o | — | — | — |
| Strip D | | | | | w | n | p | g | — | — | — |
| Strip E | | | | | u | p | g | — | — | — | — |

TABLE 1-continued

| Product | Pad |||||||||||
| --- | --- | --- | --- | --- | --- | --- | --- | --- | --- | --- | --- |
| | 1 | 2 | 3 | 4 | 5 | 6 | 7 | 8 | 9 | 10 | 11 |
| Strip F | | | | p | | g | — | — | — | — | — |
| Strip G | w | n | U | p | pH | o | s | k | b | g | — |
| Strip H | u | p | PH | o | s | k | b | g | — | — | — |
| Strip I | w | n | P | pH | o | s | k | g | — | — | — |
| Strip J | w | u | P | pH | o | s | g | — | — | — | — |
| Strip K | w | n | P | pH | o | k | g | — | — | — | — |
| Strip L | p | pH | o | s | k | g | — | — | — | — | — |
| Strip M | w | n | P | g | — | o | — | — | — | — | — |
| Strip N | u | p | PH | g | — | o | — | — | — | — | — |

In accordance with the present invention, all or substantially all of a test strip may be imaged at one time. That is, the entire test strip receives one or more test signals at substantially the same time and the resulting reflected signals are communicated to at least one detector. A test signal is a transmission of light at a given wavelength from a source. In the preferred form, light is transmitted at several wavelengths, e.g., six wavelengths in this embodiment. Although, the present invention is not intended to be limited to any specific number of wavelengths.

The received reflected signals are translated into digital data representing reflectance values, as an "image" of the test strip. Each reflectance value is a function of the wavelength of the light transmitted from the source and the make-up of the test pad from which the signal was reflected. Different test pads have different spectral signatures. A spectral signature is a plot of reflectance (e.g., as a percentage) versus wavelength for a given material. Therefore, given a wavelength and a set of spectral signatures (comprising reference reflectance values), a material (e.g., test pad) associated with a given reflectance value can be determined by comparing that reflectance value with the reference reflectance values from the set of spectral signatures for the given wavelength.

The number of pads on the test strip is determined by analysis of the different reflectance values from the imaged test strip. Knowledge of the number of test pads on a strip assists in the determination of the format of a test strip, e.g., 3.25" or 4.25". The test strip format, reflectance values, and wavelength of the source are used to determine or confirm the identification of the test strip, e.g., Strip A from Table 1 above. That is, in the preferred embodiment, for the given wavelength of the source, the reflectance values are analyzed against a set of reference reflectance values to determine the identity of pads, as discussed above, and each pad's location on the test strip. Once the individual pads are counted and spectrally identified, the test strip can be identified, or its identity confirmed, by comparison of the determined test pad information to configurations of known test strip types. Eliminated is the need for a test strip to have special identification markings. Such known types of test strips may be those available from Bayer Health Care, LLC, Roche Diagnostics, TECO or other makers. If the test strip type can not be determined, the reflectometer 100 generates a corresponding signal or alert. If the test strip type is determined by the reflectometer, the test strip type may be output, e.g., via touch screen 120.

The reflectometer 100 may be configured such that the operator initially selects or enters (i.e., identifies) a test strip type. The reflectometer would independently determine the test strip type, as a confirmation of the user entered test strip type. Otherwise, an initial user selection or entry identifying the test strip type is not needed; the reflectometer determines the test strip identity without such user input. Once the test strip identity is known or confirmed, the reflectance values can be analyzed to determine the results of the test with respect to each test pad. Consequently, eliminated is the need to manually or visually confirm the identify the test strip prior to running the test.

Figure 3A:
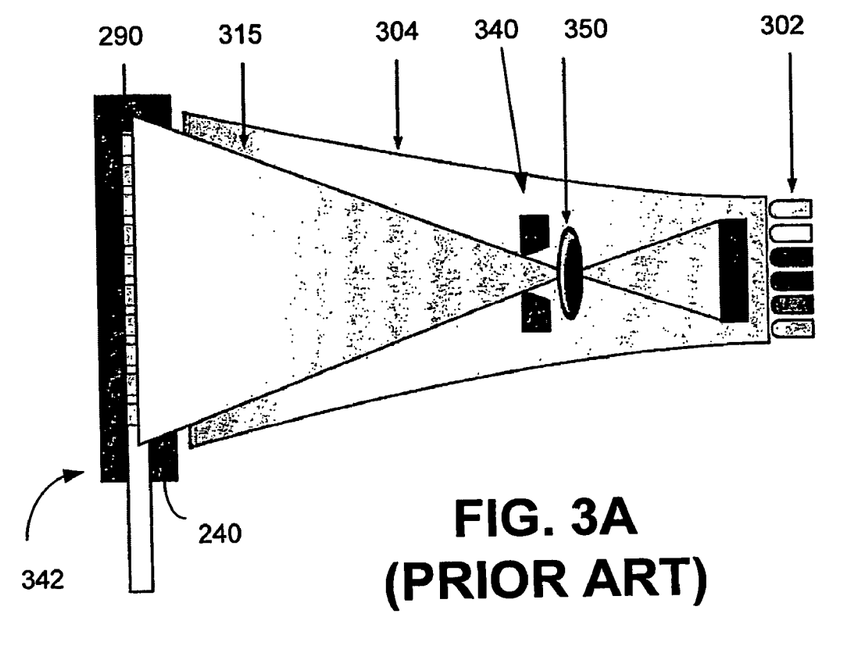
FIG. 3A and FIG. 3B are diagrams depicting the arrangement of functional elements within the spectrometer of FIG. 1.
Figure 3B:
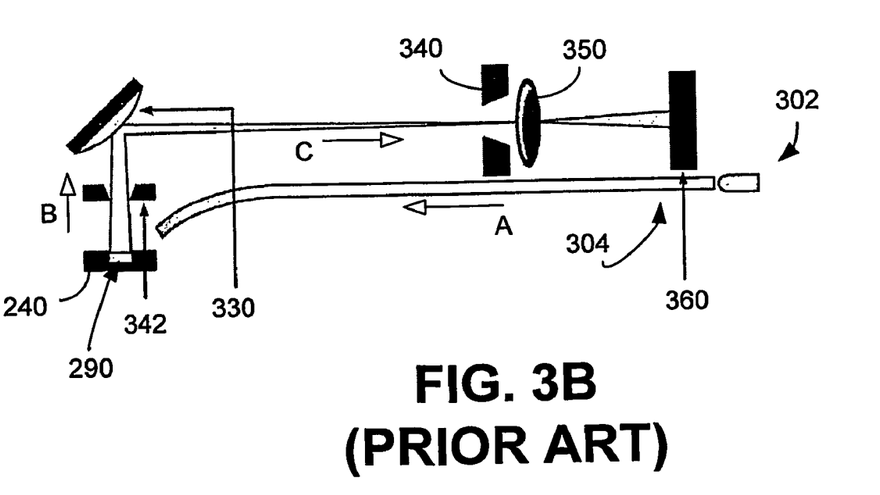

FIGS. 3A and 3B show two different views of one embodiment of various functional elements that may be used for test product imaging. A top view is shown in FIG. 3A and a side view is shown in FIG. 3B. As is shown in each of the figures, test signals are provided by transmitters 302. In the preferred form, transmitters 302 are light-emitting diodes (LEDs), preferably six, as shown in FIG. 3A, each of which transmits a different signal having a unique wavelength. In this embodiment, the signals transmitted by the LEDs are blue light at a wavelength of 470 nanometers (nm), green light at a wavelength of 525 nm, green light at a wavelength of 565 nm, red light at a wavelength of 625 nm, red light at a wavelength of 660 nm, and an infrared (IR) signal at a wavelength of 845 nm.

Test signals from LEDs 302 are transmitted through a guide 304 in the direction of arrow A. The test signals from guide 304 impinge on test strip 290 at an angle of about 45°, in the preferred embodiment. In this embodiment, test strip 290 is housed within carriage 240. Light reflected from the test strip in the direction of arrow B passes through aperture 342, after which it impinges on convex mirror 330 (not shown in FIG. 3A), which redirects and focuses the reflected signals in the direction of arrow C. In this arrangement, due to the orientation of mirror 330, the path of the reflected signals takes a 90° turn after leaving the test strip 290. The reflected signals propagating in the direction of arrow C pass through aperture 340 and converge at aspheric lens 350. Aspheric lens 350 diverges the reflected signals and the diverged reflected signals continue to propagate in the direction of arrow C. The reflected signals impinge on detector 360. As will be appreciated by those skilled in the art, the shapes and arrangement of mirrors and lenses need not specifically conform to or be limited to those shown in the illustrative embodiment of FIGS. 3A and 3B.

As previously mentioned, detector 360 receives the reflected signals, translates them into an image comprised of data representing reflectance values associated with the test pads 292, which is processed to determine the identification of the test strip type. In the preferred embodiment, detector 360 is a charge coupled device (CCD) comprised of a matrix of 2048 pixels configured to receive the reflected signals. Data from the reflected signals is recorded pixel-by-pixel as the reflectance values. Pixel data are grouped and associated with individual pads on the test strip 290. As a result, the test strip is imaged and reflectance values for each pad is determined.

Figure 4A:
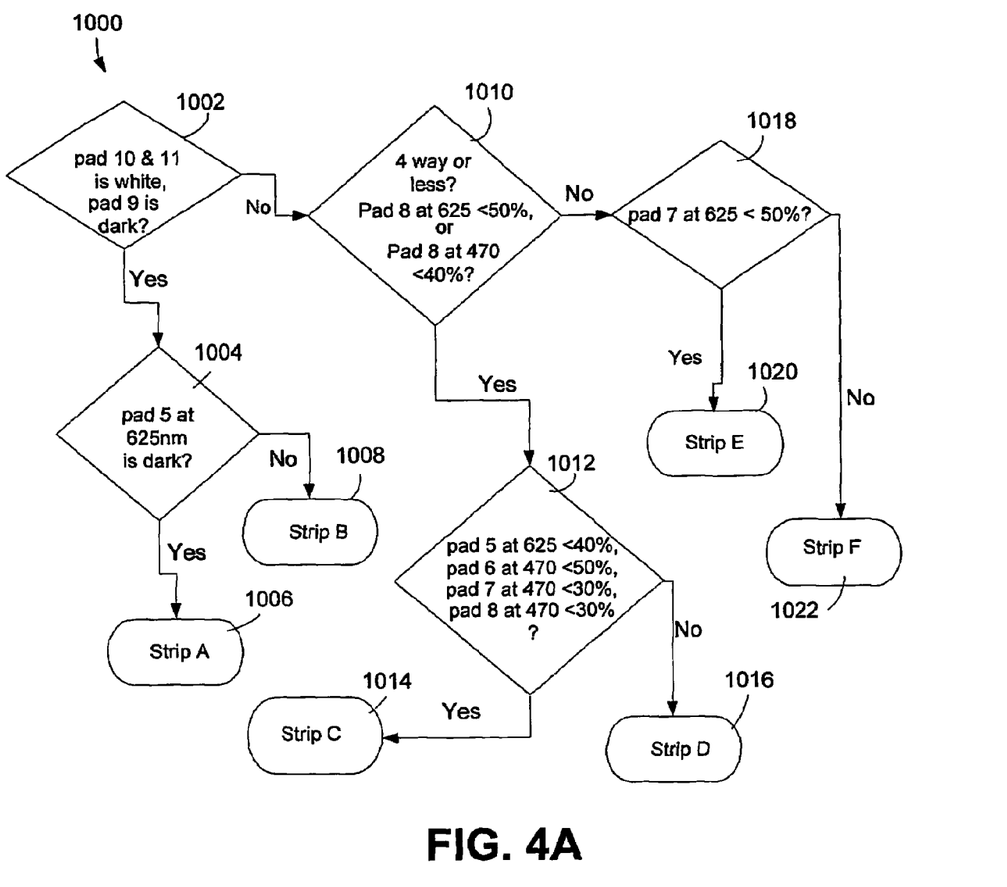
FIG. 4A is a flowchart depicting one embodiment of an algorithm for determining the identification of Bayer test strips having a 3.25 inch format.
Figure 4B:
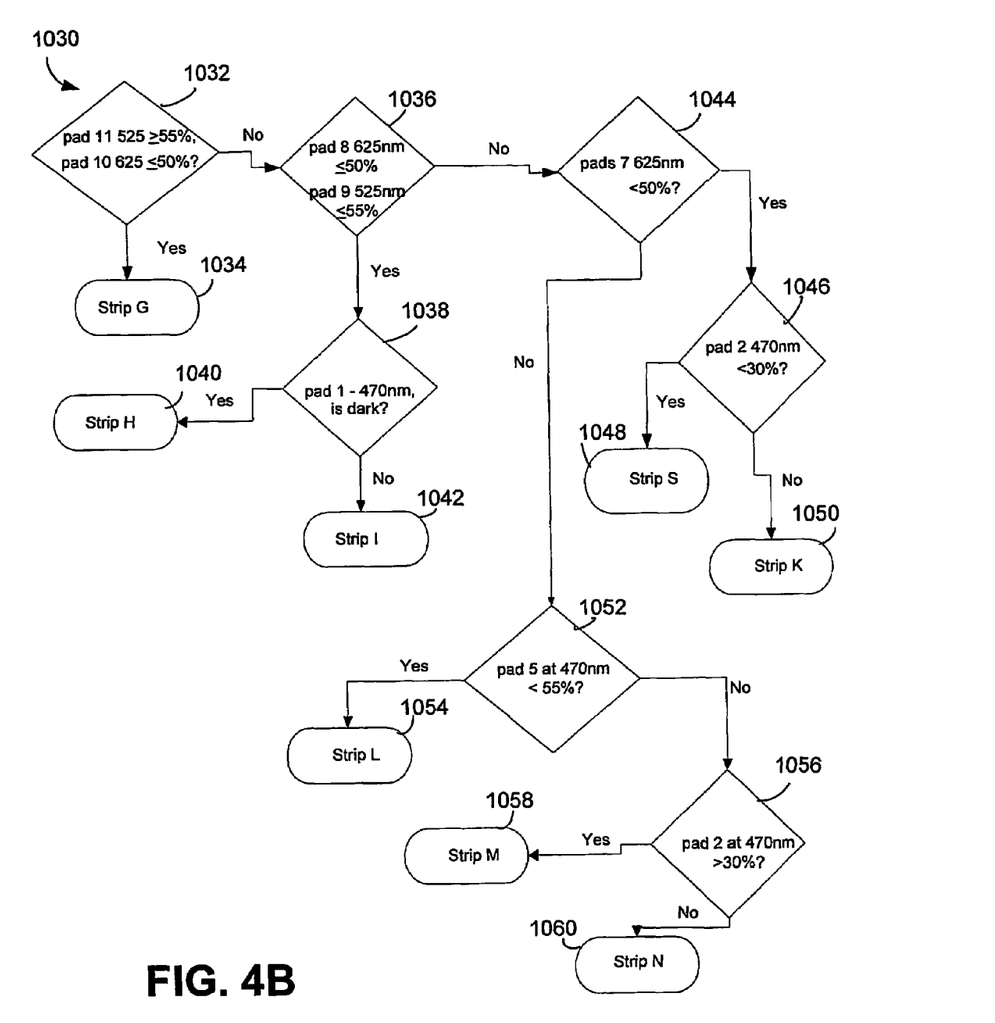
FIG. 4B is a flowchart depicting one embodiment of an algorithm for determining the identification of test strips having a 4.25 inch format.

FIGS. 4A and 4B show two logic diagrams for determining the identification of a test strip from those of illustrative Table 1 as a function of the received reflectance values. That is, FIGS. 4A and 4B are merely illustrative examples for testing a subset of possible test strips. Generally, the logic can be expanded to cover any number of commercially available or known test strips. With reference to FIG. 4A, in step 1002, the first test determines whether pads 10 and 11 are white and if pad 9 is dark. By "white", it is meant that the reflectance values for the pad are above a certain threshold value, e.g., >55%. And, by dark it is meant that the reflectance values for the pad are below a certain threshold value, e.g., <50%. If the conclusion is "yes", the process continues to step 1004, where a determination is made of whether pad 5, at a wavelength of 625 nm, is dark. If pad 5 is dark, then, as shown in step 1006, the test strip is a Strip A. If pad 5 is not dark at 625 nm, then, as shown in step 1008, the test strip is, in this example, a Strip B. This determination is made as a process of elimination as the test strip identification method works through the logic diagrams.

Returning to step 1002, if the conclusion is "no", the process continues to step 1010. In step 1010, the process determines if the reflectance value of pad 8 at 625 nm is less than 50% of the reference reflectance value ($R_{625}$) at that wavelength or if at 470 nm the reflectance value is less than 40% of $R_{470}$. The value of R differs for each wavelength, i.e., $R_{470}$, $R_{525}$, $R_{565}$, $R_{625}$, $R_{660}$ and $R_{845}$, are unique values. If the conclusion of either of those tests is "yes", the process continues to step 1012. In step 1012, a series of comparisons are made with respect to pads 5, 6, 7 and 8. This test includes determining for pad 5, at 625 nm, if the reflectance value is less than 40% of $R_{625}$, if for pad 6 at 470 nm the reflectance value is less than 50% of $R_{470}$, if for pad 7 at 470 nm the reflectance value is less than 30% of $R_{470}$, and if for pad 8 at 470 nm the reflectance value is less than 30% of $R_{470}$. If the conclusion to each of those conditions is "yes", the test strip is a Strip C, in step 1014. If the conclusion is "no", then the test strip is a Strip D, in step 1016.

Returning to step 1010, if the conclusion is "no", the process continues to step 1018. In step 1018, a determination is made with respect to pad 7 at 625 nm of whether the reflectance value is less than 50% of $R_{625}$. If the conclusion is "yes", the test strip is a Strip E, in step 1020. If the conclusion is "no" then the test strip is a Strip F, in step 1022. As will be appreciated by those skilled in the art, other tests could be performed to identify other types of test strips. FIG. 4B shows a process 1030 similar to that of FIG. 4A, but for determining the identification of a test strip of the 4.25" format. Starting in box 1032, a determination is made of whether the reflectance value for pad 11, at a wavelength of 525 nm, is greater than or equal to 55% of $R_{525}$ and if for pad 10 at 625 nm the reflectance value is less than 50% of $R_{625}$. If the conclusion to both tests is "yes" as shown in box 1034, the test strip is a Strip G. Otherwise, if the conclusion is "no", the process continues to step 1036. In step 1036, a determination is made for pad 9, at 525 nm, of whether the reflectance value is greater than or equal to 55% of $R_{525}$ and if for pad 8, at 625 nm, the reflectance value is less than or equal to 50% of $R_{625}$. If the conclusion to each is "yes", the process moves to step 1038 where a determination is made for pad 1, at 470 nm, of whether the reflectance value is less than or equal to 50% of $R_{470}$. If the conclusion is "yes", then the process continues to step 1040 where the test strip is identified as a Strip H. Otherwise, the test strip is identified as a Strip I.

If the conclusion in step 1036 is "no", the process continues to step 1044. In step 1044, if the reflectance value for pad 7, at 625 nm, is less than or equal to 50% of the $R_{625}$, the process continues to step 1046. In step 1046, if the reflectance value for pad 2, at 470 nm, is less than 30% of $R_{470}$, the process continues to step 1048, where the test strip is identified as a Strip J. If the conclusion in step 1046 is "no", the process continues to step 1050, where the test strip is identified as a Strip K.

If the conclusion in step 1044 is "no", the process continues to step 1052. In step 1052, if pad 5, at 470 nm, has a reflectance value less than 55% of $R_{470}$, the process continues to step 1054, where the test strip is identified as a Strip L. If the conclusion in step 1052 is "no", the process continues to step 1056, where a determination is made as to whether the reflectance value for pad 2, at 470 nm, is greater than 30% of $R_{470}$. If it is, the process continues to step 1058 where the test strip is determined to be a Strip M. If it is not, the process continues to step 1060 where the test strip is identified to be a Strip N. As will be appreciated by those skilled in the art, similar steps and algorithms could be included to identify other types of test strips.

The above functionality may be implemented in any of a variety of computer programs configured for storage in a memory and for execution by at least one computer processor to identify a test product having a set of test regions, in accordance with the present invention. A preferred embodiment of such a computer program comprises various functional modules that cooperatively work to control and exchange data with the various physical elements of a reflectometer as described herein, for example. These functional modules are set out here using rather generic terms, but other terms could be used and the modules could be defined differently, so long as they cooperate to identify a test product as provided herein.

Figure 5:
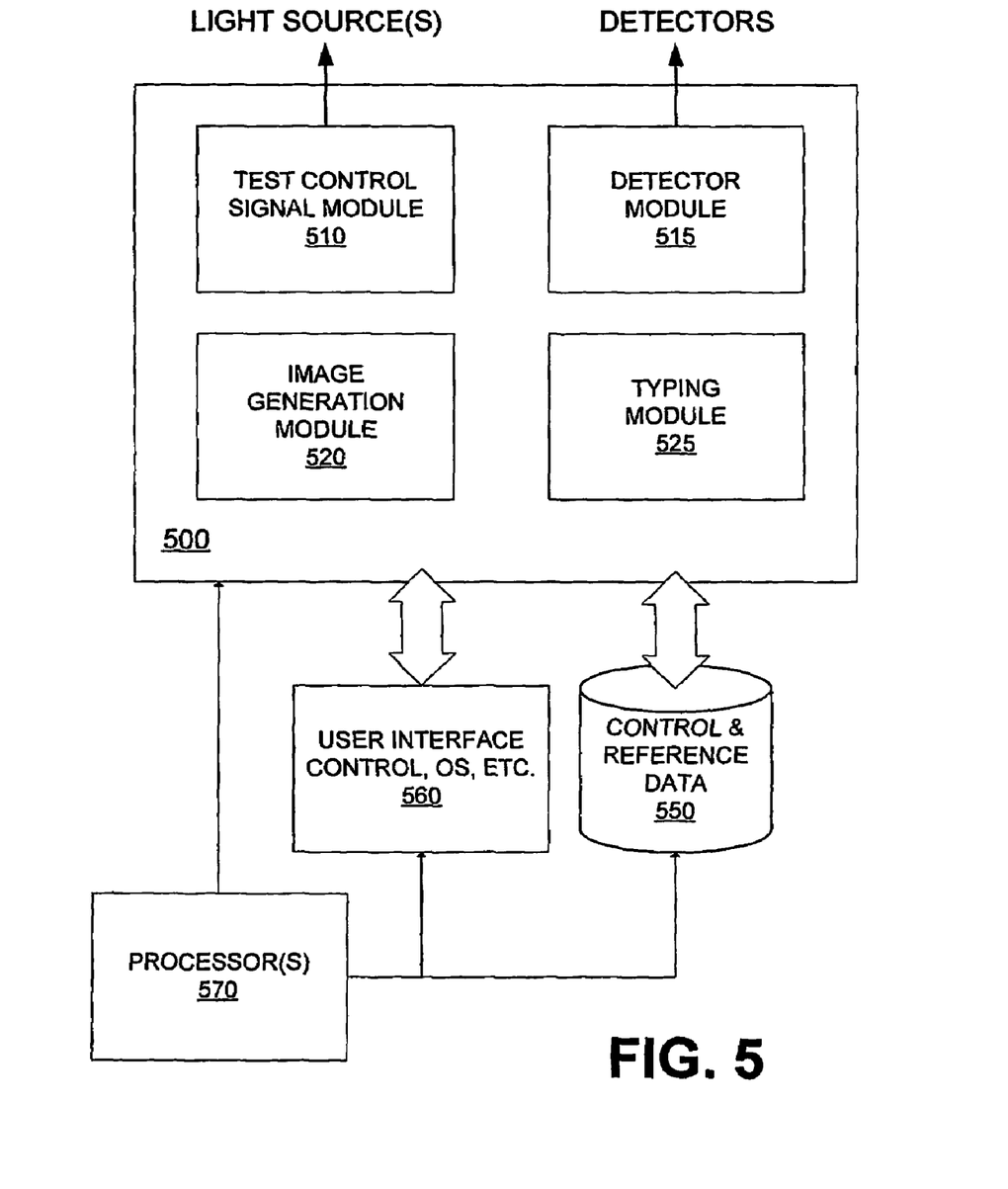
FIG. 5 is a block diagram of a computer program that may be used to implement the logic of FIGS. 4A and 4B.

FIG. 5 shows an embodiment of a computer program 500 that may be used with the device of FIG. 1, for example. The computer program 500 comprises a test signal control module 510 configured for causing a set of light sources to impinge on a set of test regions at least one test signal having a known wavelength. A detector module 515 is configured for processing signals from a detector 520 in response to detection of a set of reflected signals from the set of test regions. An image generation module 520 is configured for generating an image comprising a set of reflectance values derived from the set of reflected signals. A typing module 525 is configured for determining a test region type from the image for at least one test region from the set of test regions by comparing a reflectance value associated with the test region with a set of reference reflectance values stored in memory 550, wherein each of the reference reflectance values corresponds to the known wavelength and is associated with a different reference test region type. A typing module 525 is configured for identifying said test product as a function of a set of determined test region types.

The computer program may be implemented in any combination of hardware, software or firmware and if software, stored in at least one storage device, such as memory 550. As will be appreciated by those skilled in the art, computer program 500 will also communicate or interface with other types of hardware, software, or firmware, generally designated by block 560, such as an operating system (OS), user interface devices and communication means under control of at least one processor 570.

While the foregoing has described what are considered to be the best mode and/or other preferred embodiments, it is understood that various modifications may be made therein and that the invention or inventions may be implemented in various forms and embodiments, and that they may be applied in numerous applications, only some of which have been described herein. As used herein, the terms "includes" and "including" mean without limitation. It is intended by the following claims to claim any and all modifications and variations that fall within the true scope of the inventive concepts.

What is claimed is:

1. A method of identifying a test strip having a set of test pads, said method comprising:
   A. illuminating said set of test pads with at least one test signal having a wavelength;
   B. detecting a set of reflected signals from said set of test pads;
   C. generating an image comprising a number of test pads and a set of reflectance values derived from said set of reflected signals, and counting said number of test pads to determine a test pad count and determining a test strip format as a function of said test pad count;

D. determining a test pad type from the image for at least one test pad from the set of test pads by comparing a reflectance value associated with the test pad with a set of reference reflectance values, wherein each of said reference reflectance values corresponds to said wavelength and is associated with a different reference test pad type; and E. identifying said test strip as a function of a set of determined test pad types.

2. The method of claim 1, wherein said at least one test signal is a test signal from an LED light source.

3. The method of claim 1, wherein said at least one test signal is a plurality of test signals generated from a set of LEDs, wherein each LED in said set of LEDs is configured to transmit light at a different wavelength.

4. The method of claim 1, wherein step C includes determining a test pad reflectance value for each test pad in said set of test pads.

5. The method of claim 4, wherein step C includes determining a test pad order from said test pad reflectance values.

6. The method of claim 5, wherein step D includes selecting said set of reference reflectance values as a function of a test pad position in said test pad order.

7. The method of claim 1, wherein step B includes creating a pixel-based image of
said test strip from said reflected signals.

8. The method of claim 7, wherein said pixel-based image comprises a plurality of pixel sets and each pixel set corresponds to a different test pad.

9. The method of claim 1, further including:
F. determining a test result for the at least one test pad as a function of the reflectance value.

10. A method of identifying a test product having a test region, said method comprising:
A. illuminating said set of test pads with at least one test signal having a wavelength;
B. detecting a set of reflected signals from said test region with a matrix of pixel-based detectors and creating a pixel-based image of said test region, wherein said pixel-based image comprises a plurality of pixel sets and each pixel set corresponds to a different test area from said test region, wherein generating an image includes counting a number of test pads to determine a test pad count and determining a test strip format as a function of said test pad count;
C. determining, from said pixel-based image, a reflectance value for at least one test area from said test region;
D. determining a test product type by comparing a reflectance value associated with the at least one test area with a set of reference reflectance values, wherein each of said reference reflectance values corresponds to said wavelength and is associated with a different reference test area type; and
E. identifying said test product as a function of a set of determined test area types.

11. The method of claim 10, wherein the test product is a test strip and the test areas are test pads on the test strip.

12. The method of claim 10, wherein the test product is a reagent cassette and the test areas include one or more of a test line, control line and reference in the test region.

13. A system for identifying a test strip including a set of test pads, said system comprising:
A. media having data indicative of a plurality of reference test strips and of a set of spectral signatures, wherein each of said spectral signatures is associated with a reference test pad type and includes a reference reflectance value at each of a plurality of wavelengths;
B. a set of test signal generators configured to illuminate said set of test pads with at least one test signal having a known wavelength;
C. a matrix of pixel-based detectors, configured to detect reflected signals from said set of test pads and to create a pixel-based image of said test strip, wherein said pixel-based image comprises a plurality of pixel sets and each pixel set corresponds to a different test pad on said test strip;
D. a translator configured to determine a reflectance value for at least one test pad from said set of test pads from the pixel based image;
E. a pad typing module configured to compare said reflectance value with a set of reference reflectance values from said set of spectral signatures for said wavelength to determine a test pad type; and
F. an identification module, configured to identify said test strip as a function of a set of test pad types determined by said pad typing module and to count a number of test pads to determine a test pad count and determining a test strip format as a function of said test pad count.

14. A system for identifying a test strip including a set of test pads, said system comprising:
A. media having data indicative of a plurality of reference test strips and of a plurality of sets of reference reflectance values, wherein each set of reflectance values is associated with a reference test pad type and a reference wavelengths;
B. a set of test signal generators configured to illuminate said set of test pads with at least one test signal having a known test wavelength;
C. one or more detectors configured to generate an image of the test strip from the reflected signals;
D. a translator configured to determine a reflectance value from said image for at least one test pad from said set of test pads;
E. a pad typing module configured to compare said reflectance value with said sets of reference reflectance values for said test signal wavelength to determine a test pad type; and
F. an identification module, configured to identify said test strip as a function of a set of test pad types determined by said pad typing module and to count a number of test pads to determine a test pad count and determining a test strip format as a function of said test pad count.

15. The system of claim 14, wherein said at least one test signal is a test signal from an LED light source.

16. The system of claim 15, wherein said at least one test signal is a plurality of test signals generated from a set of LEDs, wherein each LED in said set of LEDs is configured to transmit light at different a wavelength.

17. The system of claim 14, wherein said translator is configured to determine a test pad reflectance value for each of said test pads.

18. The system of claim 17, wherein said pad typing module is configured to determine a test pad count as a function of said test pad reflectance values and said pad typing module is further configured to determine a test strip format as a function of said test pad count.

19. The system of claim 14, wherein said translator is configured to determine a test pad reflectance value for each of said test pads and said pad typing module is further configured to determine a test pad order as a function of said test pad reflectance values.

20. The system of claim 19, wherein said pad typing module is further configured to apply a selected set of reference reflectance values as a function of a test pad position in said test pad order.

21. The system of claim 14, wherein said detectors are configured to create a pixel-based image of said test strip from said reflected signals.

22. The system of claim 21, wherein said pixel-based image comprises a plurality of pixel sets and each pixel set corresponds to a different test pad.

23. The system of claim 14, further comprising:
F. a test conduct module, configured to determine a test result for the at least one test pad as a function of the reflectance value.

24. A reflectometer for identifying a test strip including a set of test pads, said reflectometer comprising:
A. media having data indicative of a plurality of reference test strips and of a set of spectral signatures, wherein each of said spectral signatures is associated with a reference pad type and includes a reference reflectance value at each of a plurality of wavelengths;
B. a set of light emitting diodes (LEDs) configured to illuminate said set of test pads with at least one test signal having a known wavelength;
C. one or more charge coupled device (CCD) detectors, configured to detect reflected signals from said set of test pads and to create a pixel-based image of said test strip, wherein said pixel-based image comprises a plurality of pixel sets and each pixel set corresponds to a different test pad on said test strip;
D. a translator configured to determine a reflectance value for at least one test pad from said set of test pads from the pixel-based image;
E. a pad typing module coupled to said one or more CCD detectors and configured to compare said reflectance value with a set of reference reflectance values for said wavelength to determine a test pad type; and
F. an identification module, configured to identify said test strip as a function of a set of pad types determined by said pad typing module and to count a number of test pads to determine a test pad count and determining a test strip format as a function of said test pad count.

25. The system of claim 24, further comprising:
F. a test conduct module, configured to determine a test result for said at least one test pad as a function of the reflectance value.

26. The system of claim 24, wherein said translator is configured to determine a reflectance value for each of said test pads.

27. The system of claim 26, wherein said pad typing module is configured to determine a test pad count as a function of said reflectance values and is further configured to determine a test strip format as a function of said test pad count.

28. The system of claim 24, wherein said translator is configured to determine a reflectance value for each of said test pads and said pad typing module is further configured to determine a test pad order as a function of said reflectance values.

29. A system for identifying a test product including a test region comprised of one or more test areas, said system comprising:
A. media having data indicative of a plurality of reference test products, including reference reflectance values and reference wavelengths for each test area, wherein for each reference wavelength there is a set of reference reflectance values;
B. a set of test signal generators configured to illuminate said test region with at least one test signal having a test wavelength;
C. one or more detectors configured to generate an image of the test region from the reflected signals;
D. a translator configured to determine a reflectance value from said image for at least one test area;
E. a typing module configured to compare said reflectance value and the test wavelength with the reference reflectance values having a reference wavelength substantially equal to the test wavelength to determine a test area type; and
F. an identification module, configured to identify said test product as a function of a set of test area types determined by said typing module and to count a number of test pads to determine a test pad count and determining a test strip format as a function of said test pad count.

30. The method of claim 29, wherein the test product is a test strip and the test areas are test pads on the test strip.

31. The method of claim 29, wherein the test product is a reagent cassette and the test areas include one or more of a test line, control line and reference in the test region.

32. A computer program product including computer-readable instructions resident in a computer-readable medium the computer-readable instructions comprising:
A. a test signal control module configured for causing a set of light sources to illuminate a set of test regions with at least one test signal having a wavelength;
B. a detector module configured for causing a detector to detect a set of reflected signals from said set of test regions;
C. an image generating module configured for generating an image comprising a set of reflectance values derived from said set of reflected signals;
D. a typing module configured for determining a test region type from the image for at least one test region from the set of test regions by comparing a reflectance value associated with the test region with a set of reference reflectance values, wherein each of said reference reflectance values corresponds to said wavelength and is associated with a different reference test region type; and
E. a test product identification module configured for identifying said test product as a function of a set of determined test region types and to count a number of test pads to determine a test pad count and determining a test strip format as a function of said test pad count.

33. A computer program product as in claim 32, wherein the test product is a test strip and the test regions are test pads.

* * * * *